United States Patent [19]

Berninger et al.

[11] Patent Number: 4,830,725
[45] Date of Patent: May 16, 1989

[54] ELECTROPHORESIS APPARATUS

[75] Inventors: Mark Berninger, Gaithersburg, Md.; Michael Schuette, Vienna, Va.

[73] Assignee: Life Technologies, Inc., Gaithersburg, Md.

[21] Appl. No.: 81,692

[22] Filed: Aug. 4, 1987

[51] Int. Cl.$^4$ ............................................. G01N 27/26
[52] U.S. Cl. ................................ 204/299 R; 204/182.8
[58] Field of Search ............ 204/299 R, 182.8, 182.9; 220/408, 410; 422/117

[56] References Cited

U.S. PATENT DOCUMENTS

| | | | |
|---|---|---|---|
| 3,129,158 | 4/1964 | Raymond et al. | 204/182.8 |
| 3,222,053 | 12/1965 | Severdia. | |
| 3,677,930 | 7/1972 | Meshbane et al. | 204/182.8 X |
| 3,819,505 | 6/1974 | Parent et al. | 204/299 R |
| 3,847,773 | 11/1974 | Snyder | 204/299 R X |
| 3,932,265 | 1/1976 | Hoefer | 204/299 R |
| 3,969,218 | 7/1976 | Scott | 204/299 R |
| 3,989,612 | 11/1976 | Kragt et al. | 204/182.8 X |
| 4,035,377 | 7/1977 | Detroy | 204/299 R |
| 4,049,534 | 9/1977 | Posner | 204/299 R |
| 4,061,560 | 12/1977 | Hannig et al. | 204/299 R |
| 4,061,561 | 12/1977 | Fletcher et al. | 204/182.8 X |
| 4,123,346 | 10/1978 | Ploix | 204/299 R |
| 4,124,470 | 11/1978 | Dahms | 204/299 R X |
| 4,142,960 | 3/1979 | Hahn et al. | 204/299 R |
| 4,151,065 | 4/1979 | Kaplan et al. | 204/182.8 X |
| 4,154,669 | 5/1979 | Goetz | 204/299 R |
| 4,187,160 | 2/1980 | Zimmermann | 204/299 R X |
| 4,190,510 | 2/1980 | Larbig | 204/180.1 |
| 4,194,963 | 3/1980 | Denckla | 204/299 R |
| 4,218,302 | 8/1980 | Dalisa et al. | 204/299 R |
| 4,234,400 | 11/1980 | Kaplan et al. | 204/182.8 |
| 4,284,491 | 8/1981 | Vesterberg | 204/299 R |
| 4,289,596 | 9/1981 | Satoh | 204/299 R X |
| 4,292,161 | 9/1981 | Hoefer et al. | 204/299 R |
| 4,323,439 | 4/1982 | O'Farrell | 204/299 R X |
| 4,325,796 | 4/1982 | Hoefer et al. | 204/182.8 |
| 4,337,131 | 6/1982 | Vesterberg | 204/182.8 |
| 4,358,358 | 11/1982 | Rhodes | 204/299 R |
| 4,374,723 | 2/1983 | Vesterberg | 204/299 R |
| 4,383,905 | 5/1983 | Richman | 204/180.1 X |
| 4,415,418 | 11/1983 | Turre et al. | 204/182.8 |
| 4,545,878 | 10/1985 | Bridges | 204/157.21 |
| 4,574,040 | 3/1986 | Delony et al. | 204/299 R |
| 4,576,693 | 3/1986 | Kreisher et al. | 204/299 R |
| 4,576,702 | 3/1986 | Peck et al. | 204/299 R |
| 4,576,703 | 3/1986 | Peck et al. | 204/299 R |
| 4,588,491 | 5/1986 | Kreisher et al. | 204/182.8 |
| 4,618,408 | 10/1986 | Malavarca et al. | 204/299 R |
| 4,622,123 | 11/1986 | Nejame, Jr. | 205/299 R |
| 4,624,768 | 11/1986 | Yoshida et al. | 204/299 R |
| 4,657,655 | 4/1987 | Smoot et al. | 204/299 R |

OTHER PUBLICATIONS

"Hoefer Scientific Instruments", (1983).
McDonell, "Analysis of Restriction Fragments of T7 DNA and Determination of Molecular Weights by Electrophoresis in Neutral and Alkaline Gels", Jnl. Mol. Biol. 110, pp. 119-146.
"Astec Band-It".

Primary Examiner—John F. Niebling
Assistant Examiner—John S. Starsiak, Jr.
Attorney, Agent, or Firm—Saidman, Sterne, Kessler & Goldstein

[57] ABSTRACT

An apparatus for casting an agarose gel and for conducting an electrophoresis process is disclosed. An electrophoresis tank supports a gel casting deck having open ends which are sealed by wedge dams to form a cavity for containing the molten agarose as it gels. The wedge dams are pulled downward by gravity into wedge-shaped slots. The weight of the wedge dams in the wedge slots presses the wedge dams against the open ends of the gel casting deck so as to provide a substantially fluid-tight seal. The gel casting deck has sidewalls which are slanted toward one another so that when the gel is submerged in buffer solution during electrophoresis, the gel's tendency to float is substantially impeded. The combs which form wells in the gel are referenced to the side of the gel casting deck itself so as to ensure uniformity and accuracy of well depth. Safety features prevent the electrophoresis tank from functioning if removed from its protective housing.

22 Claims, 2 Drawing Sheets

ELECTROPHORESIS APPARATUS

BACKGROUND OF THE INVENTION

1. Field of the Invention

This invention relates to devices for forming gels for electrophoresis, and for performing electrophoresis using those gels. More specifically, the invention relates to devices for facilitating electrophoresis in horizontally oriented gels.

2. Related Art

Electrophoretic separation of nucleic acids in agarose gels is an important technique which is commonly used in molecular biology research and genetic diagnosis.

Many devices have been designed to facilitate gel electrophoresis of biologically significant macromolecules. Some of these devices are designed so as to orient the gel vertically. Other devices are designed to orient the gel horizontally.

A vertical orientation for the gel was generally preferred for the electrophoresis of nucleic acids in such applications as nucleic acid sequencing. The disadvantages of devices employing vertical orientation of the gel caused them to be replaced for many other applications by devices in which agarose gels were cast on a horizontal surface so that the electrophoretic separation occurred in a substantially horizontal direction. To case a horizontal gel, one must seal the ends of a gel casting deck onto which the heated molten gel material is poured. The casting deck thus provides a shallow cavity in which the molten agarose can cool and gel. Furthermore, to run an agarose gel, it is necessary to have effective and uniform electrical contact between the gel and the electrophoresis buffer at the ends of the gel. Several known devices have been used to cast horizontal agarose gels.

A first approach to casting horizontal gels makes use of "wicks" of agarose case in chambers at each end of the platform upon which "separation" agarose gel is later cast. The wicks seal in the molten agarose during the casting procedure. The wicks provide an effective electrical connection between the separation gel and buffer reservoirs located on the outside of the respective wicks. An apparatus which typifies this designs disclosed in U.S. Pat. No. 4,234,400 to Kaplan et al.

Another approach adopted by designers of horizontal gel electrophoresis devices employs a removable tray (or deck) upon which the agarose gel could be cast. Certain of these devices cast a gel in an apparatus separate from that used to carry out the actual electrophoresis. Typically, the deck in which the agarose gel is cast consists of two opposing sides and two open ends which, when the gel is being used to electrophoretically separate macromolecules, will be directly exposed to the buffer. Commonly, this deck is situated between two reservoirs which contain a buffered salt solution. Electrodes are installed into the respective reservoirs to provide electrical current from a power supply. The two open ends of the deck allow effective and uniform electrical contact between the gel and the buffer. To cast the gel in the first place, however, it is necessary to seal these open ends of the deck to create a fluid-tight cavity for containing the molten agarose solution before it cooled and gelled.

To use this gel after hardening, the seals at the ends of the deck first have to be removed. A first method used to block the open ends of the gel casting deck during the gel cooling and hardening process consists of sealing the ends of the deck with an adhesive tape. The tape is peeled off before installing the gel in the electrophoresis apparatus. Unfortunately, the removal of the tape is time consuming and requires that the gel be manually picked up. Any such manipulation or other disturbance to the gel is undesirable, since agarose gels are fragile.

A second method of blocking the open ends of the casting deck during the gelation process consists of placing rectangular blocks into slots cut into the side walls of the electrophoresis apparatus. These blocks are thereby positioned against the open ends of the deck, providing a surface which seals the open ends of the deck during the casting. Unfortunately, to achieve a reliably tight seal against the ends of the deck is difficult, since the reliability of the seal in this technique is dependent on the exact positioning of the side wall slots and the exact size and shape of the rectangular blocks. This rectangular block design requires that the device be constructed with very tight manufacturing tolerances which have to be maintained throughout the life of the device. Such tight tolerance requirements cause increased manufacturing costs.

A simple and convenient means for sealing and unsealing the ends of gel casting decks is therefore desirable.

Frequently, when agarose gels of the sort described above are used to electrophorese DNA, the gel breaks free from the casting deck, possibly as the result of an accidental jostle by laboratory personnel. Having broken free from the casting deck, the gel tends to drift up off the casting deck, supported by the liquid buffer, toward one of the buffer reservoirs. If the gel begins to float toward either buffer reservoir, the electrophoresis of the DNA becomes aberrant or unpredictable, and the value of the electrophoretic analysis is accordingly reduced or lost.

It is therefore desirable to have a casting deck which substantially impedes the gel from dislodging from its casting deck and floating toward a buffer reservoir.

Another problem present in known electrophoresis devices relates to the difficulty in referencing the "combs" which are used to create "wells" in the agarose gel into which samples are placed. Many known devices are designed so that, when the teeth of the combs are inserted into the molten agarose, the combs rest on surfaces which are physically remote from the casting deck. This remote referencing results in nonuniform and inaccurate separation of the ends of the teeth from the floor of the casting deck due to unreliable fitting of adjacent parts in the apparatus. This nonuniformity and inaccuracy in the placement of the combed teeth results in the creation of wells in the gel which are commensurately nonuniform and inaccurate. At times, the teeth of combs in known devices actually contact the floor of the casting deck, so that there is no agarose seal between the well and the casting deck after the agarose had gelled. This missing agarose gel seal sometimes destroys otherwise valuable experimental results.

It is therefore desirable to have a comb reference surface which substantially guarantees the uniformity and accuracy of the depth of wells in agarose gels, and thereby ensures the presence of agarose seals at the bottom of those wells. Such a reference surface would reduce the manufacturing tolerances needed to manufacture the apparatus.

Still another problem in known devices is the danger to which laboratory personnel are exposed. Curiosity or carelessness on the part of the laboratory personnel results in injury from the high voltages involved in electrophoresis and from radioactive or otherwise dangerous chemical reactants.

It is therefore desirable to design electrophoresis devices so that, in operation, the ability of curious or careless laboratory personnel to cause injury to themselves or others is substantially reduced or eliminated.

SUMMARY OF THE INVENTION

In the present invention, the ends of a gel casting deck are sealed by means of wedge-shaped blocks which are positionable into slots cut into the side walls of the electrophoresis apparatus. The wedges are urged by their own weight against the ends of the casting deck so as to provide a reliably tight seal during the casting process. The use of wedge-shaped blocks allows more relaxed manufacturing tolerance in the shape of the blocks, and in the sidewall slot into which the wedge-shaped block rests, than would be possible using a non-wedged-shaped (e.g., rectangular) block.

The taper of the wedge slot in the sidewall is downward so that the block can easily be removed after gelation without pulling on the gelled agarose. The wedges can easily be moved away from the end of the deck, as they are lifted out of the slot.

To ensure that, once the molten agarose is poured into the casting deck and gels, the gel does not float away, the two sides of the casting deck are inclined toward one another so as to form a dovetail configuration. This dovetail configuration impedes any upward motion of the gel in the buffer solution. On the floor of the casting deck, preferably located near the dovetail walls of the deck, small indentations prevent unwanted longitudinal displacement of the gel.

To ensure uniformity and accuracy of the depth of wells in the agarose gels, provision is made for the referencing of well-forming combs to surfaces which are physically close to the floor of the gel casting deck.

To ensure the safety of laboratory personnel, as well as reduce the possibility of contamination, means are provided to orient the casting deck (if removed from a protective housing) at an angle so displaced from the horizontal that no useful electrophoretic process can occur. Curious or careless laboratory personnel are thus compelled to place the electrophoresis tank in a protective support housing. The housing in turn has a lid which prevents the hookup of electrical power necessary for the electrophoretic experiment unless the lid is closed so as to cover the electrophoresis electrodes and solution. Electrical potential cannot reach the electrodes unless the tank is inserted into the housing, allowing a switch activation means in the housing to allow a switch in the tank to conduct electricity.

BRIEF DESCRIPTION OF THE DRAWINGS

The present invention is best understood by reading the following detailed description of the preferred embodiments in conjunction with the attached drawings, in which.

DETAILED DESCRIPTION OF THE PREFERRED EMBODIMENTS

Figure 1:
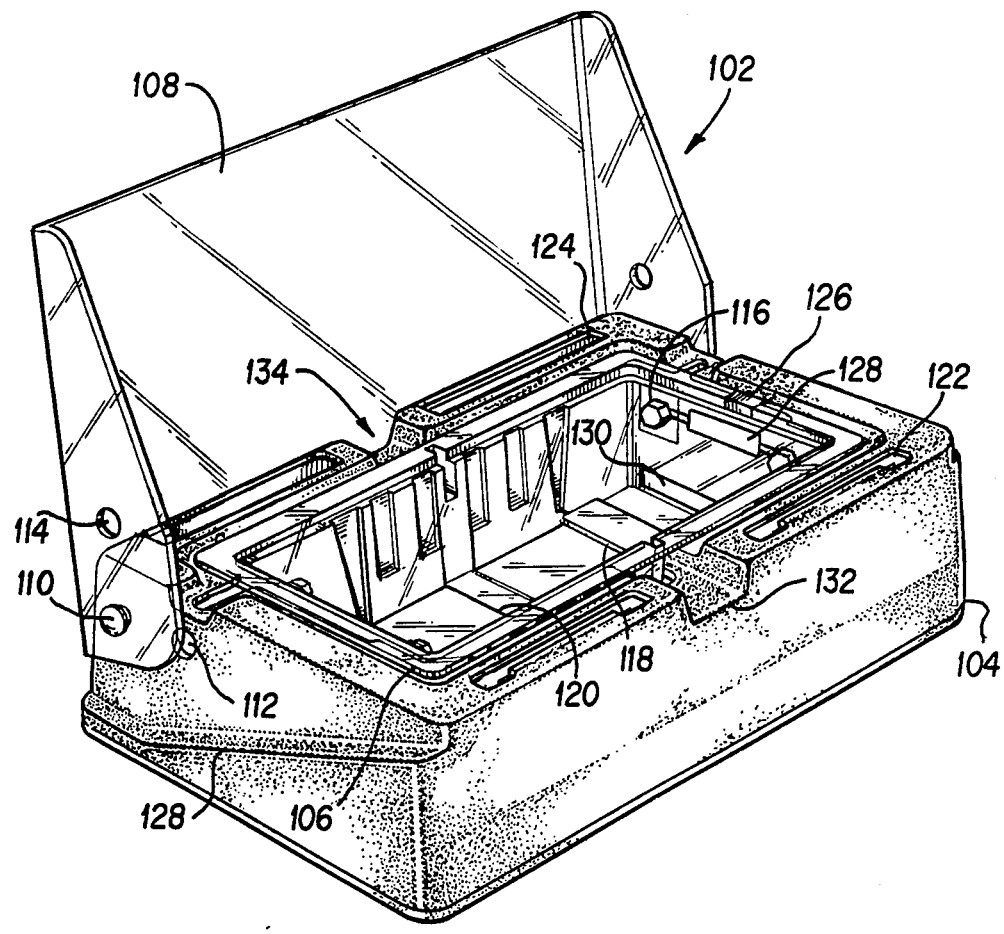
FIG. 1 is a perspective drawing of the electrophoresis apparatus according to the present invention.

FIG. 1 is a perspective view of the electrophoresis apparatus, generally indicated as 102, according to the preferred embodiment of the present invention.

Electrophoresis apparatus 102 comprises an electrophoresis tank 106 in which the electrophoresis reaction may take place. The electrophoresis tank 106 may be manufactured of 0.125 inch clear PVC, for example, but may be manufactured of any material which remains inert and impervious to the chemical reactions which are to occur within it.

The bottom of electrophoresis tank 106 has a position between deck stops 118 and 120 for a gel casting deck, to be described in more detail with reference to FIG. 2. Partial cross-section side and end views of electrophoresis tank 106 are presented in FIGS. 3 and 4 respectively.

Electrophoresis tank 106 is advantageously supported in a substantially horizontal orientation by a housing 104. Housing 104 may advantageously be manufactured of 0.125 Uniroyal Series 21 Falmouth texture, 8464 [ABS], but may be manufactured of any material which is reasonably sturdy and imervious to incidental spillage of chemicals used in the electrophoresis experiment. Optionally, a 0.125 inch white PVC sheet may be adhered to the bottom of the housing 104. This sheet (not shown) may have a fluid drainage hole close to one of the corners.

A lid 108 is attached to housing 104 at hinge 110. Lid 108 may swing down to cover electrophoresis tank 106. Lid 108 may be manufactured of a bent sheet of 0.125 inch clear acrylic, but may be manufactured of any material which is reasonably durable under normal handling.

Electrophoresis apparatus 102 has several safety features which promote the safety of laboratory personnel, while helping to prevent the contamination of the chemicals within electrophoresis tank 106.

A first safety feature relates to the design and function of lid 108. As shown in FIG. 1, a banana plug 112 is located on the side of housing 104. It is into this plug 112 (and a corresponding plug at the opposite end of the tank, corresponding to 116) that a banana jack is inserted for providing an electrical potential to electrodes such as that indicated at 130 disposed within electrophoresis tank 106 during the electrophoresis process. Since the voltages involved in most electrophoresis processes exceed 100 volts DC, there is a need to prevent curious or careless laboratory personnel from inserting their fingers into the buffer during an electrophoresis experiment in order to prevent electric shock. When lid 108 is in the open position, the side of lid 108 blocks banana plug 112 so that no banana jack may be inserted. This blockage insures that, when lid 108 is open, no potential may be present across the fluids and gel within electrophoresis tank 106.

When lid 108 is in the closed position, its bottom edge rests upon lid stop 128, and banana jack aperture 114 is thereby positioned so as to be coincident with banana plug 112. Thus, it is only when lid 108 is in the closed position that a banana jack may be inserted into banana plug 112. Once the banana jack is inserted through banana jack aperture 114 into banana plug 112, the banana jack itself prevents lid 108 from opening again.

A second safety feature ensures that electric potential cannot be applied to electrodes 130 unless electrophoresis tank 106 is properly inserted into housing 104. In electrophoresis tank 106, banana plug 116, Reed switch 128, and electrode 130 are electrically connected in a series arrangement. As is known in the art, Reed switches change state depending on the presence or absence of a magnetic field. Here, the Reed switch will close in the presence of a magnetic field, and will open in the absence of a magnetic field. Magnet 126 (hidden from direct view) is disposed in housing 104 so that, when electrophoresis tank 106 is properly inserted into the housing 104, the magnet 126 activates Reed switch 128 so that it is a closed circuit, electrically connecting banana plug 116 to electrode 130. If electrophoresis tank 106 is removed from its housing 104, magnet 126 is no longer in physical proximity to Reed switch 128. When the magnetic field from magnet 126 no longer causes Reed switch to close the circuit between banana plug 116 and electrode 130, then electrical potential cannot reach electrode 130, even when a banana jack is inserted into the outside end of banana plug 116. This arrangement ensures that no electrical potential is applied to electrode 130 when electrophoresis tank 106 is removed from housing 104.

In the preferred embodiment, a similar arrangement of an electrode, Reed switch, and magnet is disposed at the opposite end of the electrophoresis tank, connected to the inside of banana plug 112. This duplicate arrangement ensures that no electrical potential is applied to either electrode, even when a banana jack is inserted in either of banana plugs 112 or 116. Similarly, it is advantageous that banana plugs 112 and 116 be placed substantially above the anticipated level of buffer solution in the reservoirs in electrophoresis tank 106. This high placement of the banana plugs ensures that the plugs themselves do not bypass the safety feature of an open-circuited Reed switch, and function as electrodes themselves.

A third safety feature, which is designed to ensure that electrophoresis tank 106 is in fact inserted within housing 104 during the electrophoresis process, will be described below, with reference to FIG. 4.

In addition to functionality and safety, the present invention envisions convenience as a desirable feature. For the purposes of convenience, sockets are provided in the electrophoresis apparatus housing 104 for storing various removable parts which are necessary for performing the electrophoresis processes. Specifically, one or more comb storage sockets 122 are provided for the storage of combs whose teeth are inserted into the molten agarose during the gelation process so as to create wells in the agarose gel. Similarly, one or more wedge storage sockets 124 are provided to store wedge "dams" (described below, with reference to FIG. 3) when they are not in use. When the electrophoresis apparatus 102 as a whole is not in use, lid 108 may be closed atop the combs and wedges in their respective sockets 122 and 124 so as to prevent their loss or misplacement.

Housing 104 may be equipped with a finger slot 132 which facilitates the removal of electrophoresis tank 106 from the housing 104. A second finger slot 134 may optionally be located at the back of housing 104. The easy removability of electrophoresis tank 106 from housing 104 facilitates the cleaning of the various parts of the electrophoresis apparatus 102.

Figure 2:
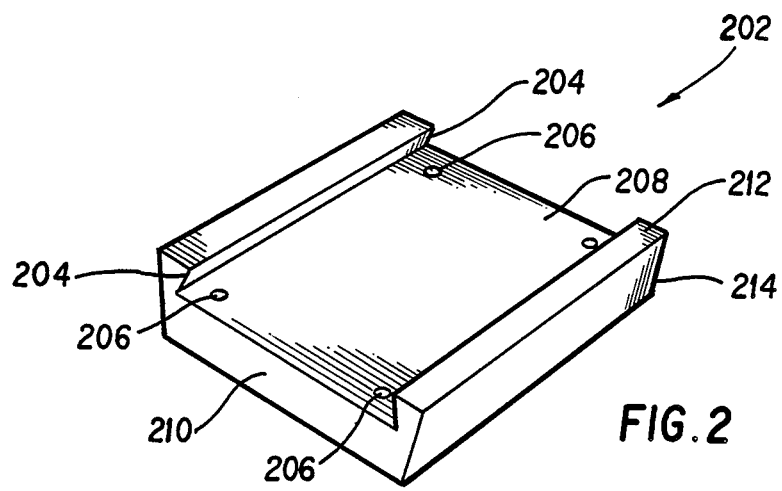
FIG. 2 is a perspective drawing of a gel casting deck to be inserted into the electrophoresis apparatus in FIG. 1.

Referring now to FIG. 2, a gel casting deck, generally indicated as 202, is shown in perspective. Gel casting deck 202 may be manufactured of clear acrylic, but may be manufactured of any material which would not wrap or otherwise deform with repeated applications of molten agarose onto its deck floor 208.

Gel casting deck 202 is designed to fit snugly into the center of the bottom of electrophoresis tank 106 (FIG. 1). Deck end 210 fits snugly against deck stop 120 (FIG. 1). The opposite end of the gel casting deck 202 fits snugly against deck stop 118 (FIG. 1). The outside wall 214 of the casting deck 202 may have a 5° draft so as to match a draft on the side walls of the electrophoresis tank 106 (FIG. 1). In this manner, the substantial immobility of casting deck 202 within electrophoresis tank 106 is ensured.

Before casting an agarose gel from molten agarose, wedge "dams" 302 (FIG. 3) are slid into position to snugly fit against deck ends 210. Then, molten agarose is poured onto deck floor 208 and is retained by dovetail walls 204 and by the wedge dams (not shown in FIG. 2). Once the gelation process has been completed, the wedge dams are removed and a buffer is added to electrophoresis tank 106 to a level which may barely submerge the agarose gel. The gel casting deck according to the preferred embodiment of the invention demonstrates its utility in preventing the movement of the agarose gel in the buffer.

In the preferred embodiment of the gel casting deck 202, the inner walls 204 are slanted inward at a perceptible angle (for example, 5°) which is exaggerated in FIG. 2 for purposes of demonstration. After the molten agarose gels, the gel has a trapezoidal shape when viewed from the end. This trapezoidal's top surface is shorter than its bottom surface. During the electrophoresis process, when the gel is partially or totally submerged in buffer, the gel's tendency to float upward is arrested by the dovetail walls 204.

After wedge dams 302 (FIG. 3) have been removed for the electrophoresis process and the buffer partially or totally immerses the agarose gel, the tendency of the gel to move horizontally in a longitudinal direction (that is, toward one end of the casting deck) is prevented by indentations 206 which are present at various locations on deck floor 208. Indentations 206 are preferably located adjacent dovetail walls 204. These indentations, typically on the order of 0.04 inches deep, fill with molten agarose as it is poured onto deck floor 208. When the agarose gels, the agarose which was present in the indentations 206 prevents the horizontal motion of the gel, since the relatively gentle forces which tend to make the gel move horizontally are insufficient to shear off that portion of the gel which filled indentations 206.

Together, dovetail walls 204 and deck floor indentations 206 provide assurance from above and below, respectively, that the agarose gel will not be displaced when immersed in buffer.

Figure 3:
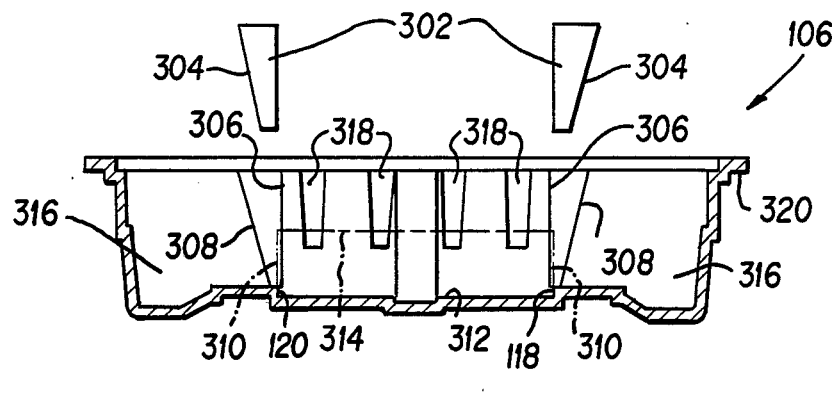
FIG. 3 is a partial cross-section side view of an electrophoresis tank to be used to the electrophoresis apparatus of FIG. 1.

Referring now to FIG. 3, the preferred embodiment of the electrophoresis tank 106 (FIG. 1) is portrayed in a partial cross-section side view. Also illustrated in FIG. 3 are the wedge dams 302 which have been referred to above. The proper position of gel casting deck 202 (FIG. 2) is shown in FIG. 3 by the dotted line whose top and ends are indicated as 314 and 310, respectively. The gel casting deck rests on deck support 312, and is held in place by fitting snugly against deck stops 118 and 120. The position for casting deck 202

(FIG. 2) as defined by dotted lines 310 extends beyond the vertical edge 306 of the wedge slot by a small amount, typically on the order of 0.03 inches. This extension beyond edges 306 is exaggerated in FIG. 3 for purposes of demonstration. Liquid buffer is inserted into buffer reservoirs 316 to a level which may approximately match the top of the agarose gel in the gel casting deck, approximately even with line 314. Cut into the side walls of electrophoresis tank 106 are a plurality (for example, four) of comb slots 318. Also cut into the side walls of electrophoresis tank 106 are the wedge slots defined by vertical edges 306 and slanted edges 308.

Typically, a 15° draft of the slanted surface 304 of wedge dams 302 has been found to be an acceptable choice. The same draft should define the slanted edge 308 of the wedge slots which receive the wedges 302. A draft of 1°-2° for comb slots 318 has also proven to be workable.

Wedge dams 302 may be manufactured of a number of materials, including clear acrylic, aluminum, or Delrin (TM of Dupont Corporation). It is highly desirable that the material exhibit a high thermal conductivity so that when the wedge dams are in place against the gel casting deck, the heat from the molten agarose is quickly absorbed by the wedge dams. This quick absorption of thermal energy causes the molten agarose to gel, forming a gel seal between the wedges and the casting deck which prevents the molten agarose from leaking into buffer reservoirs 316.

In the gelation process before the electrophoresis experiment, wedge dams 302 are inserted into the wedge slots defined by edges 306 and 308 until the wedges can slide down no further. The limit of how far wedges 302 may slide is determined by slanted slot edge 308 and by the end 310 of the gel casting deck. The present invention contemplates that the wedges 302 do not need to contact the vertical edges 306 of the wedge slot. Gravity pulls the wedges as far down into the wedge slots as possible. This constant pull of gravity, linked with a common draft angle of wedge slanted surface 304 and slanted edge 308 of the wedge slot work together to ensure that wedges 302 are reliably and firmly pressed against deck ends 310. Whereas the vertical edge of wedges 302 and deck ends 310 must be manufactured so that they have matching faces, the fact that gravity assists in pressing the wedges against the deck ends 310 implies that much greater manufacturing tolerances may be employed using wedges than when using rectangular inserts. Most conveniently, the vertical edges of wedges 302 and deck ends 310 are manufactured so that they have planar faces.

The present invention contemplates that the gelation process and the electrophoresis process may be performed without any intervening disturbance to the delicate agarose gel. Many known devices had required that the gelation process may be performed in a separate apparatus than that in which the electrophoresis process was performed.

The fact that dams 302 are wedge-shaped allows them to be removed after gelation by merely sliding them away from the gel casting deck along slanted edge 308 of the wedge slot without disturbing the gel. This feature is an improvement over the rectangular dams of known systems. When those rectangular dams were pulled up vertically, friction between the surface of the rectangular dam and the end of the agarose gel would sometimes cause damage to the delicate gel. This potential damage to the gel is averted in the preferred embodiment of the present invention by the fact that the surface of wedge dams 302 are pulled immediately away from the edge of the gel as they are drawn up the slanted edge 308 of the wedge slots.

A lip 320 which may traverse substantially the entire perimeter of electrophoresis tank 106 is provided to ensure that, when the tank 106 is inserted in housing 104 (FIG. 1), the gel casting deck 202 resting on deck support 312 is maintained in a substantially horizontal position. Maintenance of a substantially horizontal position has been found to be necessary for meaningful results in many electrophoresis applications.

Figure 4:
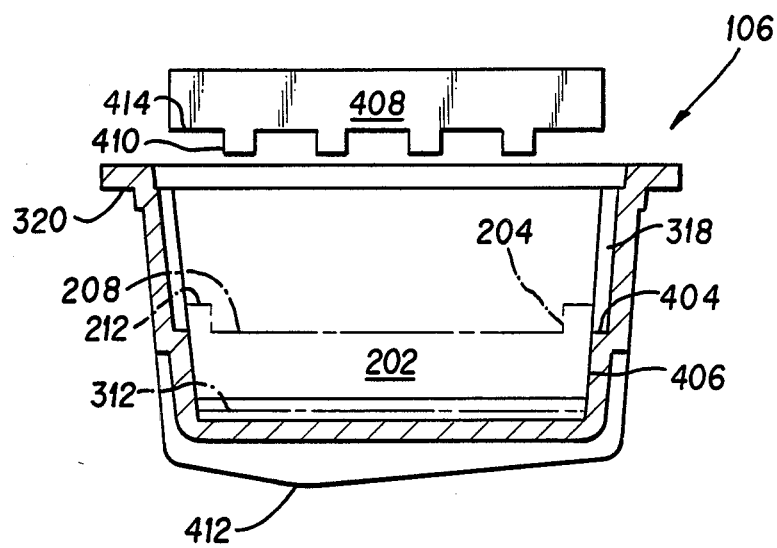
FIG. 4 is a partial cross-section end view of an electrophoresis tank to be used in the electrophoresis apparatus of FIG. 1.

Referring now to FIG. 4, the preferred embodiment of the electrophoresis tank 106 (FIG. 1) is portrayed in a partial cross-section end view. Also indicated in FIG. 4 are a properly situated gel casting deck 202 (shown in dotted lines) and a comb 408.

Comb 408 may be manufactured of Teflon (TM of DuPont Corporation) or Delrin (TM of Dupont Corporation), or of any other material which is heat resistant and smooth.

Deck support 312 is shown as a dotted line to indicate that casting deck 202 is positioned between deck stops 118 and 120 (FIG. 3). Deck stops 118 and 120 ensure that casting deck 202 does not move in a direction perpendicular to the plane of FIG. 4. Gel casting deck 202 rests on deck support 312. Casting deck 202 fits snugly in position against the tank sidewalls 406. Tank sidewalls 406 and the outside walls of casting deck 202 have a common draft, for example, 5°, to ensure that the casting deck 202 is substantially immobilized.

Deck floor 208, dovetail walls 204, and wedge dams 302 (not illustrated in FIG. 4) form a cavity into which the molten agarose is poured. During the gelation process, one or more combs 408 are positioned into the electrophoresis tank so that the teeth 410 of the comb 408 are partially inserted into the molten agarose. After gelation, the combs 408 are removed, leaving walls in the agarose gel into which, samples are inserted for the electrophoresis process.

It is important to the reliability of the experimental results that there be an agarose seal at the bottom of each well in the gel. This implies that the positioning of the teeth 410 of comb 408 must be reliably controlled so as to produce wells of uniform and proper depth. As comb 408 is positioned inside electrophoresis tank 106, there are several ways in which a proper reference may be chosen. It is more reliable, according to the present invention, to rest reference edge 414 of comb 408 on top reference edge 212 of the casting deck 202.

It would also have been possible to rest the comb's reference edge 414 against some other surface which is not a part of casting deck 202. This was the practice in many known systems. For example, the electrophoresis tank 406 could have been designed so that the bottom face 404 of comb slot 318 was higher than top reference edge 212 of casting deck 202. If this were the case, comb 408 would have to be designed so that its teeth 410 would extend exactly the right amount beneath this bottom face 404 (assuming bottom face 404 were higher than as illustrated in FIG. 4). Because of slight nonuniformity or mismatching of the casting deck 202 to the electrophoresis tank 106, using the bottom face 404 of the comb slots 318 would not provide as reliable a reference for the positioning of the comb 408.

No such positioning problems are present if top reference edge 212 of the casting deck 202 is used to support the comb at its reference edge 414. Once properly designed casting decks 202 and combs 408 have been manufactured to within reasonable physical tolerances, the requirements for uniform and accurate well depths have been met.

FIG. 4 also illustrates a kilter structure 412 which is designed to cause electrophoresis tank 106 to sit at a nonhorizontal angle when resting on a horizontal surface. Kilter structure 412 is not uniform about a center line of the electrophoresis tank 106. When the electrophoresis tank is removed from the protective housing 104 (FIG. 1), there is no simple means by which the electrophoresis tank 106 can maintain the deck floor 208 of casting deck 202 in a substantially horizontal position.

Kilter structure 412 may have either a flat bottom or a curved (ellipsoidal) bottom. A flat-bottomed kilter structure would cause the electrophoresis tank 106 to rest solidly at a non-horizontal angle. A curved kilter structure would additionally cause the entire electrophoresis tank 106 to tend to rock about an angle which is not horizontal.

The present invention provides this kilter structure to frustrate the attempts of curious or careless laboratory personnel to conduct electrophoresis experiments in an electrophoresis tank 106 which is not contained within protective housing 104 (FIG. 1). The requirement that deck floor 208 be horizontal derives from the poor experimental results to be expected when the deck is not horizontal. The frustration which the curious or careless laboratory personnel experience in the electrophoresis tank with a kilter structure 412 causes them to rely on the stabilizing lip 320 which orients the electrophoresis tank 106 in a substantially horizontal position when it is properly inserted in housing 104 (described above, with reference to FIG. 1). Once the tank 106 is properly inserted in housing 104, the safety feature provided by lid 108 (FIG. 1) further ensures that no electrophoresis experiment can be performed while there is any appreciable danger of laboratory personnel inserting their fingers into the buffer solution.

Although the present invention is specially suitable for the formation of agarose gels and subsequent electrophoresis processes which employ that gel, it can be used in any application where it is desirable to form a hardened substance from its molten state, and secure that hardened substance during the performance of a chemical experiment which may be chemically or electrically dangerous. Thus, the scope of the invention should not be limited by the exemplary embodiments described above, but should be defined only in accordance with the following claims.

What is claimed is:

1. An apparatus for forming a gel and for safely performing an electrophoresis process involving the gel, said apparatus comprising:
   (a) an electrophoresis tank having a substantially horizontal orientation during operation, comprising:
     gel casting deck positioning means;
     at least one pair of wedge slots;
     at least one reservoir for containing a buffer solution for the electrophoresis process;
     electrodes for receiving electrical potential generated outside said tank and applying said potential to said buffer solution;
     kilter means for orienting said electrophoresis tank in a non-horizontal orientation when placed directly on a horizontal surface; and
     safety switching means comprising, in electrical series connection:
       (1) an electrical connector for receiving said externally generated electrical potential;
       (2) a series switch; and
       (3) said electrodes;
   (b) a gel casting deck for placement into said electrophoresis tank, comprising:
     dovetail walls which slope toward one another so as to retain the gel;
     a deck floor comprising at least one indentation;
     at least one deck end with faces; and
     at least one top reference edge for supporting a comb;
   (c) at least one wedge dam for sliding into said at least one wedge slot and contacting said faces of said at least one deck end to form a gel casting volume defined by faces of said at least one wedge dam, said dovetail walls, and said deck floor, wherein said faces of said at least one wedge dam are physically matched to said faces of said at least one deck end;
   (d) a housing comprising a switch control and comprising an inner edge for supporting said electrophoresis tank and orienting said gel casting deck in a substantially horizontal orientation within said electrophoresis tank;
     wherein said switch control causes said series switch to be a closed circuit when said electrophoresis tank is inserted in said housing; whereby application of electrical potential to said electrodes is made substantially more inconvenient when said electrophoresis tank is not inserted in said housing; and
   (e) lid means attached to said housing having an open position in which said tank is exposed and said electrical connector is covered for preventing application of said electrical potential to said electrodes and a closed position in which said tank is covered and said electrical connector is exposed for permitting application of said electrical potential to said electrodes.

2. A gel casting deck for forming a gel from a molten substance, for use in an electrophoresis process, said gel casting deck comprising:
   a deck floor comprising at least one indentation for accepting the molten substance to substantially impede motion of the gel; and
   a plurality of dovetail walls attached to respective edges of said deck floor, which dovetail walls are slanted toward one another to substantially impede motion of the gel.

3. The gel casting deck according to claim 2, wherein:
   said indentations are located adjacent said dovetail walls.

4. An apparatus for forming a gel from a molten substance, said apparatus comprising:
   a gel casting deck for receiving and holding the molten substance during a gelation process, said deck having open ends;
   sealing dams for sealing said open deck ends; and
   dam receiving slots located near said open ends, each said dam receiving slot comprising a contact surface which is oriented neither vertically nor horizontally;
   wherein each said dam has a matching face with a respective one of said open ends, and wherein each said dam receiving slot physically contacts one of said sealing dams, and, as said sealing dam is pulled by gravity further into said dam receiving slot, said contact surface contacts said sealing dam and thereby exerts an at least partially horizontal force against said sealing dam in the direction of a respective one of said open ends to form a substantially fluid-tight seal.

5. The apparatus according to claim 4, wherein: said dams and said slots are wedge-shaped.

6. The apparatus according to claim 4, wherein: said gel casting deck comprises dovetail walls which slope toward each other so as to substantially prevent motion of the gel.

7. The apparatus according to claim 6, wherein: said gel casting deck further comprises a deck floor which has at least one indentation for accepting the molten substance to substantially impede motion of the gel.

8. The apparatus according to claim 4, wherein: each said dam comprises material which readily conducts heat; wherein said dam facilitates the gelation of the molten substance to form a fluid-tight seal between said dam and said open end of said gel casting deck.

9. A method of forming a gel from a molten substance, said method comprising the steps of:
inserting sealing dams into receiving slots which are formed in a tank and which have contact surfaces which are oriented neither vertically nor horizontally, so that said contact surfaces of said receiving slots physically contact said sealing dams, and, as said sealing dams are pulled by gravity further into said receiving slots, said contact surfaces thereby exert an at least partially horizontal force against said sealing dams in the direction of said open ends so as to form a substantially fluid-tight seal;
pouring the molten substance into a cavity defined by a deck floor and walls of said gel casting deck, and faces of said dams;
allowing the molten substance to cool and thereby form the gel; and
removing said dams from said slots so that contact between the gel and said dams is discontinued near the beginning of the removing step.

10. The method according to claim 9, wherein said inserting step comprises:
inserting wedge-shaped sealing dams.

11. An apparatus for safely performing an electrophoresis separation, said apparatus comprising:
a housing;
a tank comprising a kilter means which effectively prohibits maintaining a substantially horizontal orientation of said tank when said tank is placed on a flat surface, outside said housing, to thereby orient the tank in a substantially non-horizontal orientation, which effectively prevents optimum performance of the electrophoresis separation; and
lid means, attached to said housing, having an open position for preventing energy necessary for performance of the electrophoretic separation from entering said tank so as to prevent the electrophoretic separation from being optimally performed, and having a closed position for allowing energy necessary for performance of the electrophoresis separation to enter said tank so as to allow said electrophoresis separation to be performed;
wherein said tank is substantially covered by said lid means when in said closed position.

12. The apparatus according to claim 11, wherein: said kilter means comprises an asymmetric base which causes a gel casting deck within said tank to be oriented in a position which is not horizontal when said tank is placed directly on a horizontal surface.

13. The apparatus according to claim 11, wherein: said tank comprises electrodes; and
said lid means, when in said open position, prevents application of an electric potential across said electrodes, thereby preventing said energy necessary for performance of the electrophoretic separation from entering said tank.

14. A single apparatus for performing both a gelation process and an electrophoresis process, said apparatus comprising:
a gel casting deck for receiving a molten substance and holding said substance during the gelation process;
an electrophoresis tank comprising
slots, each said slot having a contact surface with an orientation which is neither vertical nor horizontal; and
two buffer reservoirs,
said electrophoresis tank for supporting said gel casting deck between said two buffer reservoirs, said two buffer reservoirs receiving and storing buffer for the electrophoresis process; and
sealing dams which press against respective open ends of said gel casting deck with a pressure having a horizontal component;
wherein said dams are insertable in said slots during the gelation process so that said slots physically contact said sealing dams, and, as said dams are pulled by gravity further into said slots, said contact surfaces contact said sealing dams to thereby exert an at least partially horizontal force against said sealing dams in the direction of said open ends to form a substantially fluidtight seal; and
wherein said dams are removable from said slots for the electrophoresis process.

15. The apparatus according to claim 14, wherein: said dams and said slots are wedge-shaped.

16. The apparatus according to claim 14, wherein: said gel casting deck comprises dovetail walls which slope toward each other to substantially impede motion of said gel.

17. The apparatus according to claim 14, wherein: said gel casting deck further comprises a deck floor which has at least one indentation which accepts said molten substance to substantially impede motion of said gel.

18. The apparatus according to claim 14, wherein: said dams comprise material which readily conducts heat;
whereby said dams facilitate gelation of said molten substance to form a fluid-tight seal between said wedge dams and said open ends of said gel casting deck.

19. A method for performing both a gelation process and an electrophoresis process, said method comprising the steps of:
inserting sealing dams into receiving slots formed in a tank to comprise contact surfaces which are oriented neither vertically nor horizontally, so that said contact surfaces physically contact said sealing dams, and, as said sealing dams are pulled by gravity further into said receiving slots, said contact surfaces thereby exert an at least partially horizontal force against said sealing dams in the direction of said open ends so as to form a substantially fluid-tight seal;

pouring a molten substance into a cavity defined by a deck floor and walls of said gel casting deck, and faces of said dams;

cooling said molten substance to form a gel;

removing said dams from said slots so that contact between said gel and said dams is discontinued near the beginning of the removing step;

filling reservoirs adjacent to open ends of said gel casting deck with a buffer; and applying an electrical potential across electrodes inserted in said buffer to cause the electrophoresis process.

20. The method according to claim 19, wherein said inserting step comprises:

inserting wedge-shaped sealing dams.

21. An apparatus for safely performing an electrophoretic separation, said apparatus comprising:

a housing comprising a switch control; and a tank for fitting into said housing for performance of the process, said tank comprising, in electrical series connection:
  (a) an electrical connector for receiving externally generated electrical potential;
  (b) a series switch; and
  (c) an electrode;

wherein said switch control causes said series switch to be a closed circuit when said tank is inserted in said housing so that said switch control is located in a predetermined relation to said series switch;

whereby application of electrical potential to said electrode for performance of the electrophoretic separation is made substantially more inconvenient when said tank is not inserted in said housing.

22. The apparatus according to claim 21, wherein:

said switch control comprises a magnet; and said series switch comprises a Reed switch.

* * * * *